United States Patent [19]
Lang et al.

[11] Patent Number: 6,071,593
[45] Date of Patent: *Jun. 6, 2000

[54] CERAMIC PACKING WITH CHANNELS FOR THERMAL AND CATALYTIC BEDS

[75] Inventors: Ko C. Lang, Agoura Hills, Calif.; Jun Huang, Lanzhou, China

[73] Assignee: Lantec Products, Inc., Agoura Hill, Calif.

[*] Notice: This patent is subject to a terminal disclaimer.

[21] Appl. No.: 09/091,928

[22] PCT Filed: Dec. 23, 1996

[86] PCT No.: PCT/US96/20261

§ 371 Date: Jun. 24, 1998

§ 102(e) Date: Jun. 24, 1998

[87] PCT Pub. No.: WO97/24572

PCT Pub. Date: Jul. 10, 1997

Related U.S. Application Data

[63] Continuation-in-part of application No. 08/630,958, Apr. 5, 1996, Pat. No. 5,851,636.
[60] Provisional application No. 60/009,876, Dec. 29, 1995.

[51] Int. Cl.[7] .................................. B32B 3/28; F28F 3/00
[52] U.S. Cl. ..................... 428/167; 428/120; 428/166; 428/172; 156/89.22; 156/290; 156/292; 165/166
[58] Field of Search ..................... 428/120, 137, 428/167, 172, 192, 166, 99; 156/60, 290, 292, 302.4, 89.22; 165/9.1, 166, 167, 1.8; 261/DIG. 72

[56] References Cited

U.S. PATENT DOCUMENTS

| | | | |
|---|---|---|---|
| 4,705,097 | 11/1987 | Mita et al. | 165/4 |
| 4,771,826 | 9/1988 | Grehier et al. | 165/166 |
| 5,310,593 | 5/1994 | Tsujimoto et al. | 428/166 |
| 5,658,537 | 8/1997 | Dugan | 428/172 |
| 5,851,636 | 12/1998 | Lary et al. | 428/167 |

*Primary Examiner*—Donald Loney
*Attorney, Agent, or Firm*—Marvin E. Jacobs

[57] ABSTRACT

A ceramic packing element (500) is formed from a stack of ceramic plates (502) having parallel ribs (504) forming parallel grooves therebetween. The grooves are formed into channels by being contacted with the surface of an opposed plate. The ribs (504) may engage the end surfaces of ribs on an adjacent plate or may be interleaved with the ribs (504) of an opposed plate to form smaller channels. The plates (502) are adhered to each other by firing a stack of plates (502) in the green state or by adhering cured plates (502) by means of an inorganic adhesive such as sodium silicate. Pressure drop and cracking may be reduced, mass transfer and heat efficiencies increased by enlarging the inlets (542) to the channels and by providing perforations through the plates between the ribs (504). Elements may be preassembled into larger units before placement in a column by wrapping metal bands around an assembly of elements.

12 Claims, 8 Drawing Sheets

CERAMIC PACKING WITH CHANNELS FOR THERMAL AND CATALYTIC BEDS

CROSS-REFERENCE TO RELATED APPLICATION

This application is a continuation-in-part of application Ser. No. 08/630,958 filed Apr. 5, 1996 now U.S. Pat. No. 5,851,636 and of provisional application Ser. No. 60/009,876 filed Dec. 29, 1995.

TECHNICAL FIELD

The present invention relates to processes utilizing beds of ceramic packing to heat and/or react a body of fluid or act as a carrier for a catalyst and, more particularly, this invention relates to such processes utilizing improved ceramic packings for the beds.

BACKGROUND OF THE INVENTION

Regenerative thermal beds are used to capture and store heat from a first hot stream of fluid and then to transfer the heat to a second cold body of fluid before it is reacted such as by combustion, oxidation, reduction or other chemical process whether reacted in the presence or absence of a catalyst.

Originally gravel was used as the packing for the bed. Ceramic saddles and Raschig rings have been utilized for decades. As the saddles and Raschig rings randomly pack into the heat exchanger shell, they may locally stack in an orientation that will block flow. The flow is non-uniform throughout the bed of material and the pressure drop through a heat exchanger containing saddles, gravel or rings is relatively high, usually about 10 inches of water. Furthermore, the locally blocked areas may trap fluid which can contaminate the flow of second fluid or can be exhausted to the environment.

Recently, the use of monolithic columns of ceramic material for the heat exchanger columns in a regenerative thermal oxidizer system for cleaning combustion gas has been disclosed in U.S. Pat. No. 5,352,115. The monolithic columns have a lower pressure drop and reduce contamination experienced with random packing of saddles or rings.

Monolithic columns carrying a layer of catalyst are also used in catalytic processes to synthesize or convert gaseous streams to other products and in the treatment of exhaust gases from combustion engines or from industrial processes. The ceramic columns are coated with catalyst materials, such as rare earth metals. However, it is expensive to manufacture monolithic columns. Furthermore, monolithic columns are rigid and brittle. After repeated cycles of heating and cooling, the column can develop stress cracks and break or shatter into small pieces. The column becomes inoperative requiring replacement of the monolithic element. This can be quite expensive in the case of columns coated with noble or rare earth metals or metallic compounds containing platinum or palladium, rhodium, etc. Also, the channels in monolithic columns are gas-tight leading to no lateral dispersion of the gas flowing in the channels.

STATEMENT OF THE INVENTION

A column having similar architecture to a monolithic column is provided by the invention at a fraction of the cost of manufacturing a monolithic column. Instead of manufacturing the column as a homogenous, unitary body, the column is formed by stacking a plurality of ceramic plates. The ceramic plates may be cured or may be in the green, uncured state. The plates have grooves formed between ribs. When the plates are stacked with the ribs and grooves parallel to the ribs and grooves on an opposing plate, an element is formed having a plurality of channels extending through the element.

The ribs on the plate can be adhered to the opposed surface. If the opposed surface is planar and the ribs have the same elevation, the opposing surface contacts the end faces to form channels. The channels can be gas tight or can allow fluid to transfer laterally depending on the continuity of the bond between opposed surfaces. The volume and cross-section of the channel will be defined by the volume and cross-section of the groove. The plates can have one flat side and one grooved side. The plates can be flat and have regular or irregular polygonal shapes such as a square, rectangular, triangular, pentagonal, hexagonal or circular. The plates can have a regular undulating cross-section or a repeating polygonal cross-section. The plates can be the same size or can increase in size and/or decrease in size in the stack. The plates can be curved into a closed cylinder and each plate will have a diameter larger than the preceding plate by the thickness of the preceding plate. All the grooves are preferably parallel to each other so that the plates can be stacked with the columns in alignment. The grooves can all be parallel to a set of opposed side walls or the grooves can be at an angle such as 30 to 60° to a set of opposed end walls.

The size of the plates and of the elements formed from the plates depends on the intended utility of the elements. If the elements are to be used in a catalytic automotive reactor, the elements are stacked end to end and side by side to form a column. The elements are usually rectangular and are formed of square plates. The plates can be from 0.5 inch to 12 inches usually 1 to 4 inches in height and width. The thickness of the plates can be from 0.01 to 1.0 inches, usually 0.04 to 0.1 inch. The height of the elements can be from 0.5 inches to 50 inches, usually from 1 inch to 12 inches.

If the elements are to be used as random packing in a tower, the elements are preferably polygonal in shape and usually have a diameter from 0.2 to 5 inches, generally from 0.5 to 3 inches. The grooves can be curved, triangular or rectangular in cross section. The top of the ribs can be pointed, flat or rounded. A flat top is preferred when the larger contact surfaces are bonded to form a closed channel. The grooves are preferably as small as possible and as closely spaced as possible. Usually the grooves will be from 0.01 inch to 1.0 inches in depth and width, preferably from 0.04 to 0.5 inches.

Another configuration for the element is one in which instead of the end of a rib being secured to the end face of an opposed rib or planar surface, one or more ribs can be disposed in a single groove in the opposed surface. The end of the rib(s) extends to the bottom surface of the groove, dividing the groove into 2 or more mini-channels. This provides an easy and reliable method to decrease the size of the channels without the need to cast or extrude plates with very small grooves.

The elements of the invention contain about the same amount of ceramic material as an equivalently sized monolithic element. However, manufacturing costs are considerably less. The ribbed plate can be produced by stamping, casting or extrusion. The plates are cut into the desired shape and stacked in the green or fired state into the shape of an element. The elements formed from green, uncured plates are manufactured by firing the stack of green plates.

When the stacks are fired, the portions of the ribs in contact with the opposed ribs or wall fuse together. However, the many points that the ribs do not adhere act as stress relievers that accommodate the expansion and contraction of the plates and prevent the ribs or plates from cracking. This may form cracks between the channels. However, since the process gases are flowing in the same direction there is no loss of efficiency. In fact mass transfer efficiency appears to be enhanced by allowing transverse flow of gas between channels. The sharp edges on the openings between channels can disturb the boundary layer, thus increasing mass transfer. Mass transfer and stress relief could be further enhanced by providing apertures in the wall of the plates. Both the lateral spread of fluid between channels and the apertures contribute to lowering the pressure drop in the column. The repetitive cycling of the ceramic columns can result in cracks developing at the inlet to the column. This source of cracking can be reduced and pressure drop can be further lowered by widening the channels at their inlets suitably by removing a short length of rib. Dispersion of gas between channels also appears to improve connective flow.

Elements can also be formed by first firing the plates. The cured plates are then stacked into an element and stabilized by adhering the pre-fired elements with adhesive or by binding the stack with bands or wrappers. The bands or wrappers can be metal or a fugitive material such as an organic plastic film such as polyethylene or Saran wrap. The fugitive organic materials are vaporized during initial heating of the heat exchanger or column of elements. However, vaporization of organic adhesive such as an epoxy and/or the organic film adds carbon oxide pollutants to atmosphere. It is preferred to use an inorganic refractory adhesive such as silicate water glass adhesive to adhere the plastic. Stacking of the elements into an ordered column can be facilitated by binding a plurality of the elements into a multi-element structure by aligning elements side by side and top to bottom in a stack and binding the stack together by adhesive or by mechanical binding means such as wire, wire mesh, metal clips or metal bands.

The ceramic plates and elements are generally formed from refractory clays generally containing such constituents as $S:O_2$, $Al_2O_3$, Mgo, CaO, $K_2O_2$, etc. The ceramic element is inert to the gases passing through the regenerative heat exchanger and remains solid at the highest temperature achieved during the process.

A test was conducted comparing a column formed from elements formed of ribbed plates according to the invention stacked with their channels aligned to a monolithic column having the same surface area. Surprisingly, the yield was 20% higher when using the stacked elements of the invention. It was expected that the yield would be lower since the irregular surfaces of the channels formed from the cast elements would increase flow resistance and decrease yield. Perhaps the rough surfaces of the channels perturbs or disturbs the boundary layer next to the surfaces and increases mixing and reaction between the gases flowing in the boundary layer.

Even though the elements formed by firing green plates after assembly into an element provides stress relief at points where the plates do not adhere it is found that elements formed from pre-fired plates perform as well and result in even less stress cracking. Furthermore, it is much cheaper to first fire the plates and assemble them later. Also the rigid fired plates are easier to handle than the soft green plates. Also the fixed in place and rigid ribs in a fired plate can be pressed together without deforming the ribs or plate. The soft moldable ribs in a green plate can bend and stretch when handled or placed under force.

These and many other features and attendant advantages of the invention will become apparent as the invention becomes better understood by reference to the following detailed description when considered in conjunction with the accompanying drawings.

DETAILED DESCRIPTION OF THE INVENTION

Figure 1:
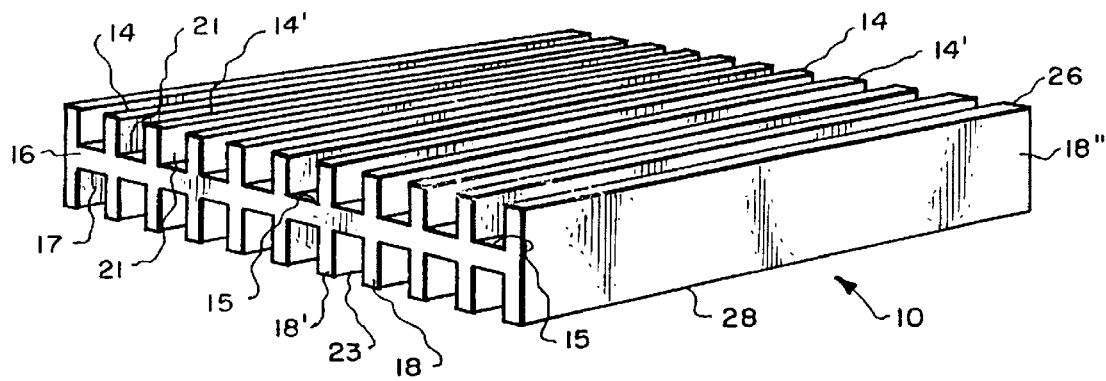
FIG. 1 is a perspective view of a first embodiment of a ribbed plate according to the invention.
Figure 2:
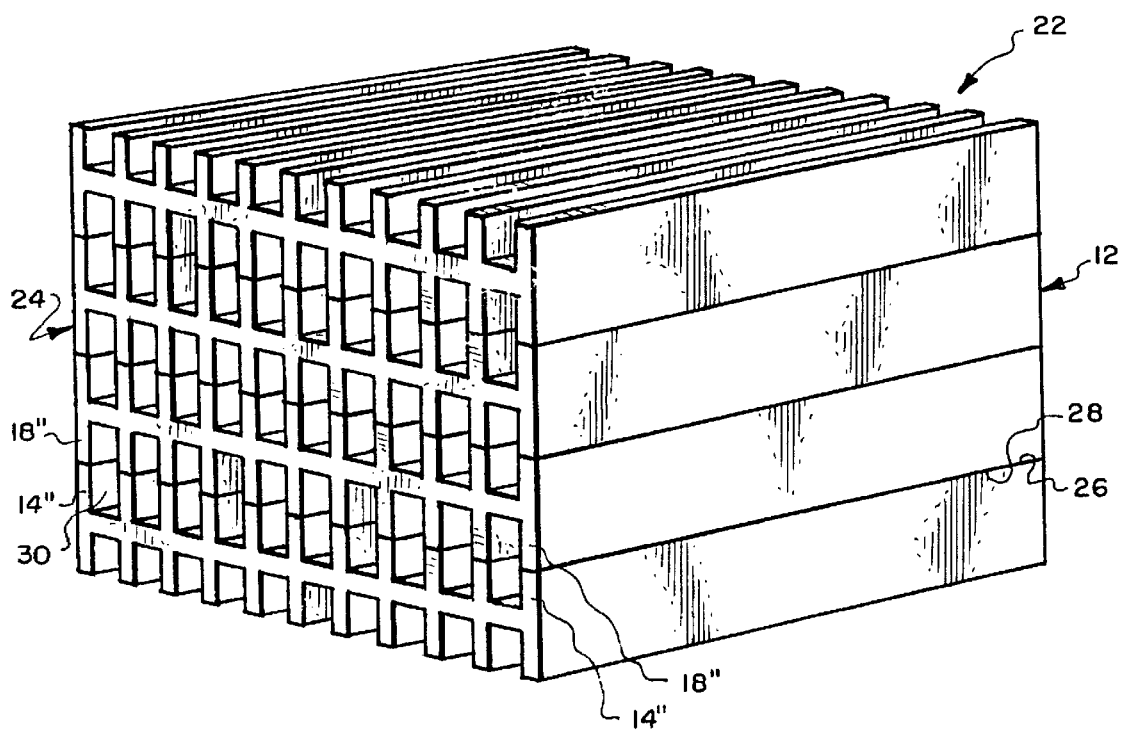
FIG. 2 is a perspective view of an element formed from a cured stack of a plurality of the ribbed plates shown in FIG. 1.

Referring now to FIGS. 1 and 2, a plate 10 is shown which can be in the green state or fired to the cured state. Cured plates can be stacked and adhered together by adhesive or by mechanically holding the stacked plates together such as by plastic wrappers or ties, bands, metal clips, etc. Plates 10 in the green or fired state can be stacked to form an element 12 as shown in FIG. 2.

Plate 10 contains a plurality of parallel ribs 14 extending from the top surface 15 of central member 16 and a plurality of parallel ribs 18 extending from the bottom surface 17 of the central member 16. Grooves 21, 23 are formed between adjacent ribs 14, 14' and 18, 18'. The opposed end faces 26, 28 of end ribs 14" and 18" join to form end walls 22, 24. The end faces 26, 28 of opposed and adjacent intermediate ribs 14, 18 join to form channels 30 having the combined volume of grooves 21 and 23. The channels 21, 23 may be closed. Preferably, the gas can leak through the intersections of end faces 26, 28 to the adjacent channel. As previously discussed, instead of stacking the plates 10 such that the opposed ends 26, 28 of ribs 14, 18 are adjacent, the plates can be stacked with the ribs 14, 18 entering the opposed grooves 21, 23 to form two channels out of each groove.

Figure 3:
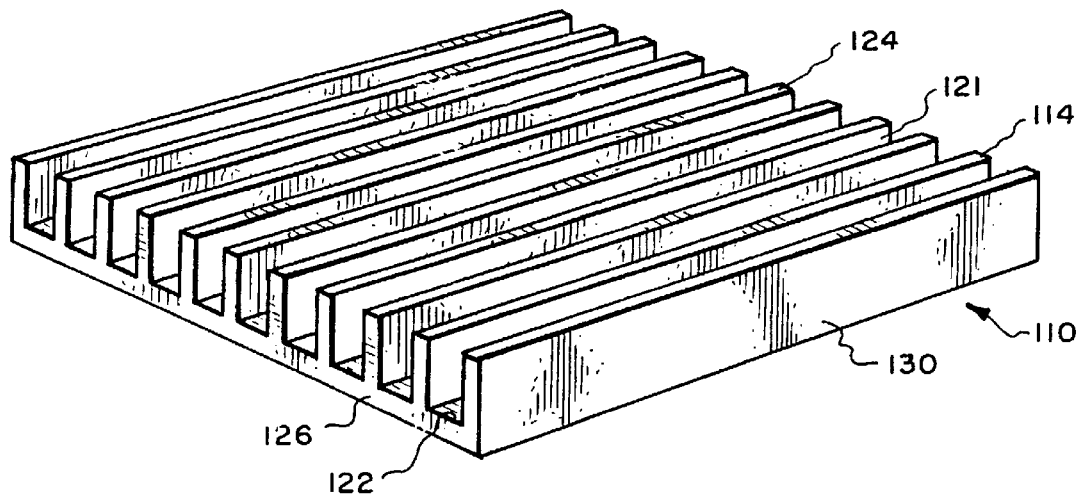
FIG. 3 is a perspective view of another embodiment of a ribbed plate according to the invention.
Figure 4:
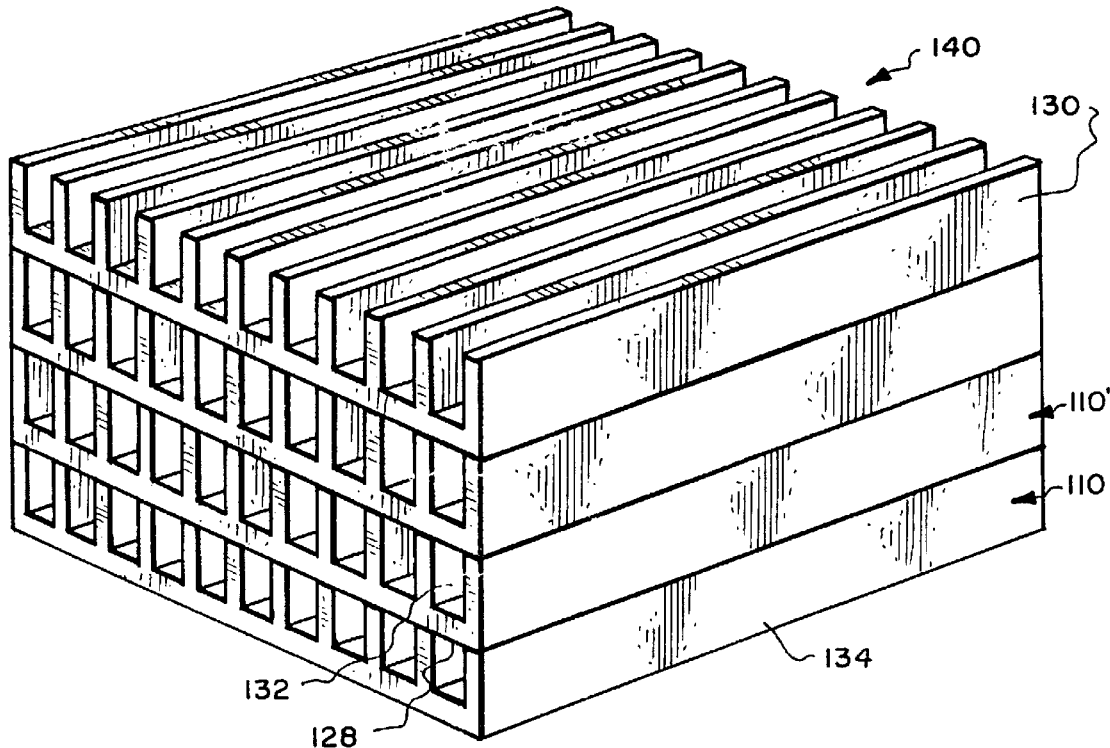
FIG. 4 is a perspective view of an element formed from a cured stack of the ribbed plates shown in FIG. 3.

Referring now to FIGS. 3 and 4, in a second embodiment of the invention, the plates 110 contains ribs 114 and grooves 121 extending from the top surface 122 of the support member 126 of the plate 110. The plates 110 are shown stacked with the end faces 124 of the ribs 114 attached to the rear face 128 of the opposed plate 110' to form an element 140. The rear face 128 closes the grooves 121 between ribs to form channels 132. The end ribs 130 join together to form a closed end wall 134.

Some of the plates 114 could also be stacked with the opposed ribs facing and joined to each other to form larger channels, not shown, or some of the plates could be stacked with the ribs entering the grooves and adhered to the bottom of the grooves to form smaller channels.

Figure 5:
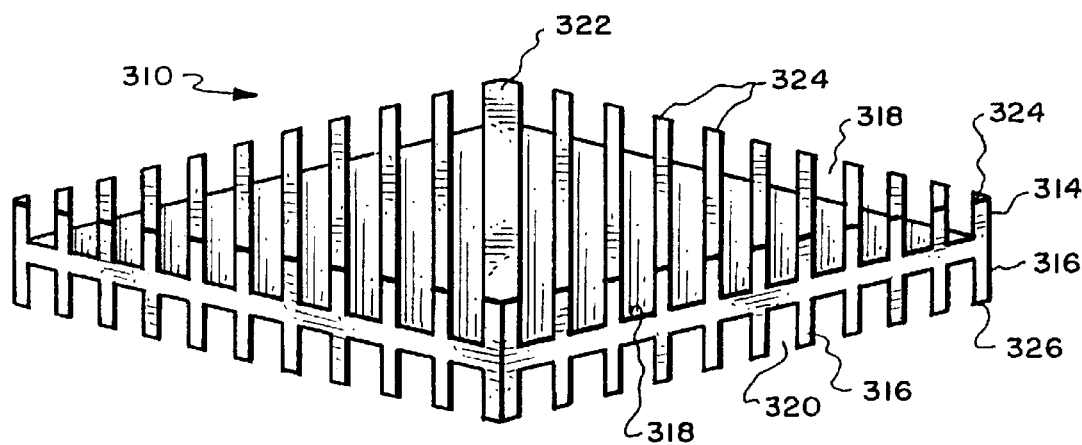
FIG. 5 is a perspective view of a further embodiment of a ribbed plate.
Figure 6:
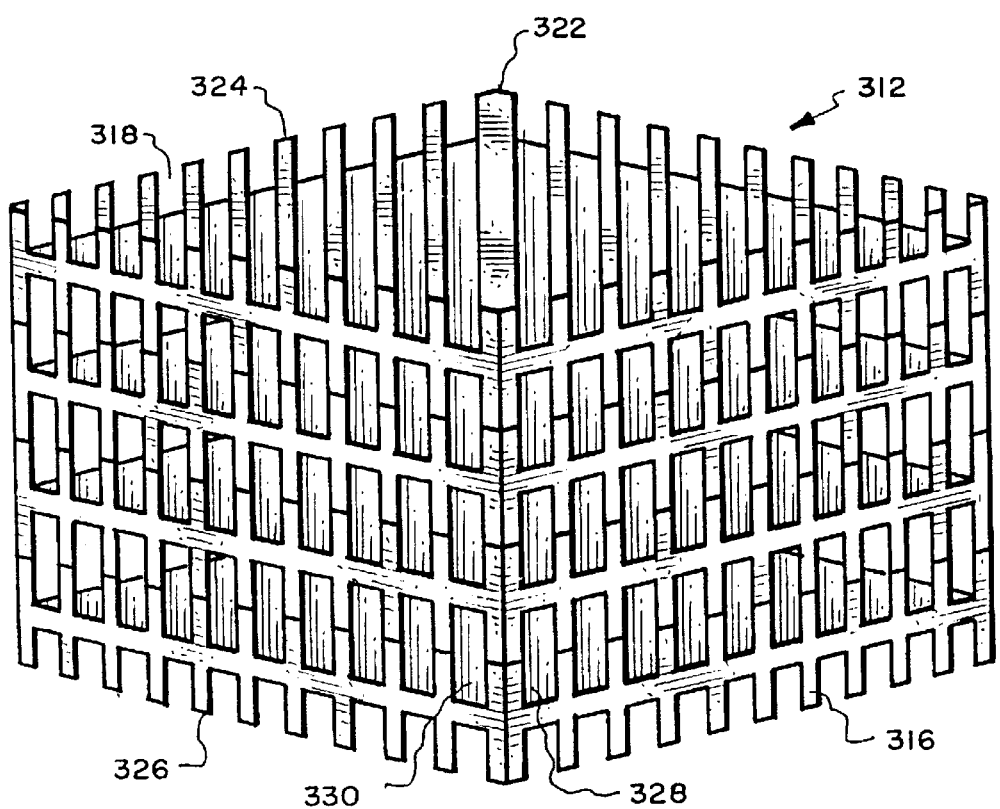
FIG. 6 is a perspective view of a cured stack of plates shown in FIG. 5 in the form of an element.

Referring now to FIG. 5 and 6, a third embodiment of a plate 310 and element 312 is illustrated. The ribs 314, 316 and grooves 318, 320 are formed parallel to a central diagonal rib 322. The end faces 324, 326 of the ribs 314, 316 in element 312 are shown in engagement forming channels 328, 330. The ribs could also be interleaved with the grooves to form smaller channels as shown in FIG. 7.

Figure 7:
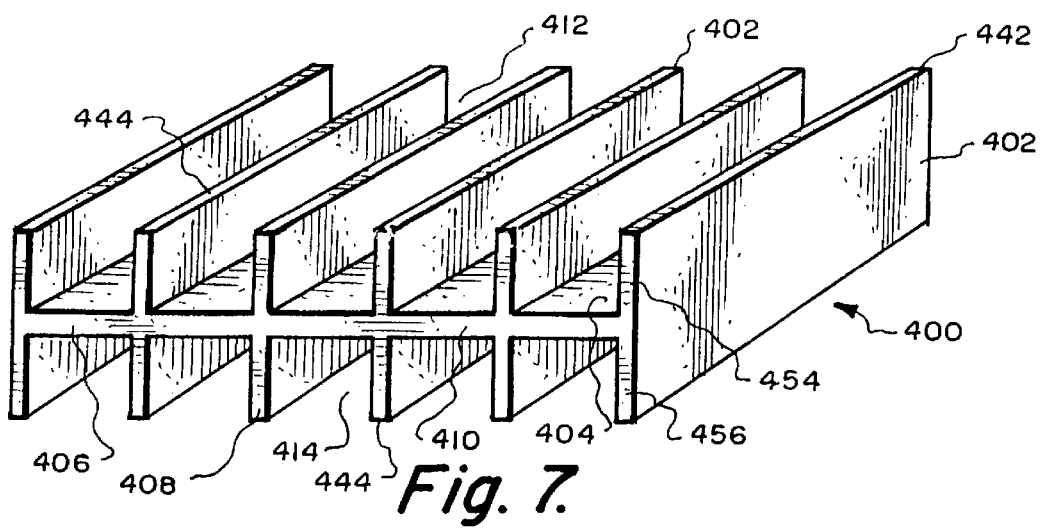
FIG. 7 is a perspective view of still another embodiment of a ribbed plate.

The plate 400 shown in FIG. 7 contains a plurality of parallel ribs 402 extending from the top surface 404 of the central member 406 and a plurality of parallel ribs 408 extending from the bottom surface of 410 of the central member 406. In order to form a planar side wall 430, an opposed plate 424 contains one less rib 418', 420' on each side of the central member 428 than the plate 400. The first rib 421, 422 of the plate 424, on each side of the central member 428 is indented ½ groove 432 from the side edge 436. The ribs 402, 408 are narrower than the grooves 412, 414 on the plate 400 and the ribs 418, 420 on the plate 424 are narrower than the grooves 437, 438, preferably occupying no more than ⅓ the distance between adjacent ribs 402, 408 or 418, 420.

Figure 8:
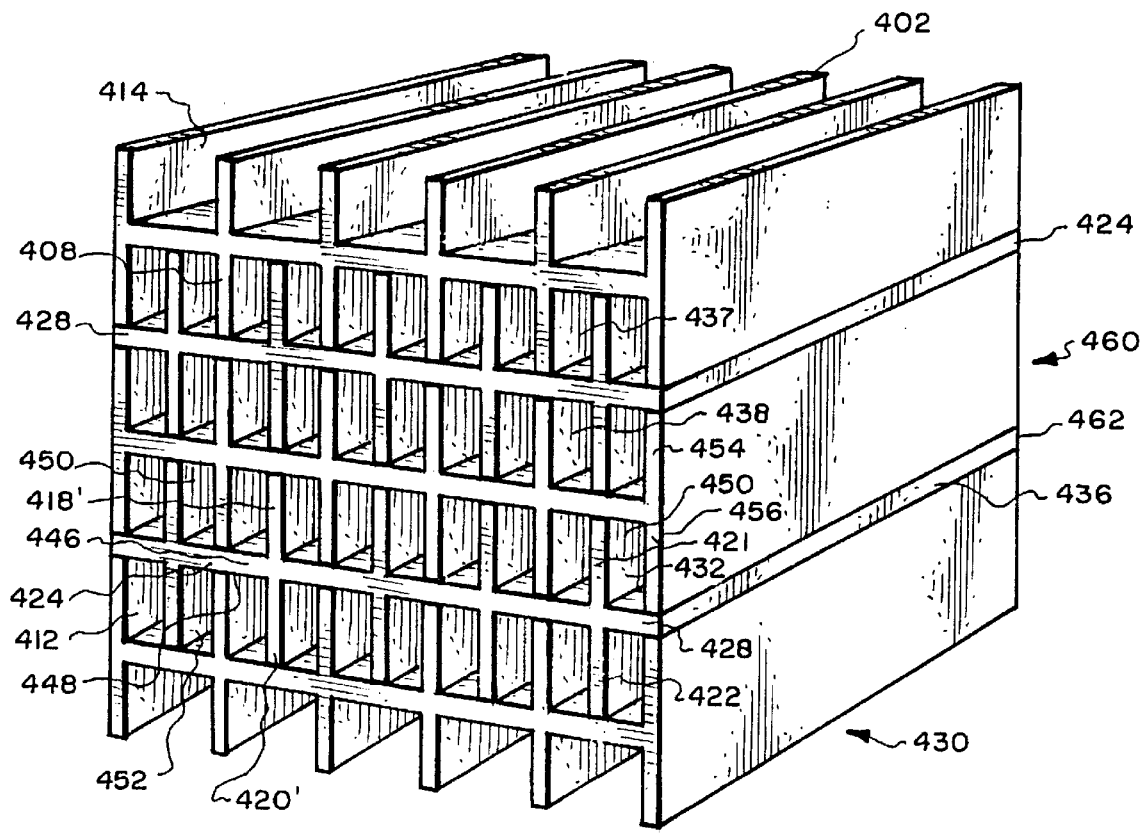
FIG. 8 is a perspective view of a cured stack of plates with the ribs of one plate as shown in FIG. 7 disposed in the grooves in an opposed plate dividing the groove into smaller channels.

As shown in FIG. 8, an element 460 is assembled by disposing the ribs 402, 408 into the grooves 437, 438 of an opposed plate 424 with the end faces 442, 444 of the ribs 402, 408 seated on the bottom surfaces 446, 448 of the opposed grooves 437, 438. The ribs 402, 408 divide each groove 437, 438 into 2 channels 450, 452. The end ribs 454, 456 close the open ends of the plates 424 to form the end small channel 462. An assembly of uncured plates is fired to form an element 460. The plates 400 and 424 can be pre-fired, assembled into a stack 460 and joined into an element by adhesive or by mechanical holding measures as previously disclosed.

The plates 400, 424 need not have ribs extending from each surface. The back surfaces can be planar. The back surfaces can be adhered to end surfaces of ribs or to the back of another plate. The grooves may accept more than one rib such as 1 to 4 ribs. The element may contain all plates interleaved to form smaller channels or some plates may have regions of interleaved ribs and grooves and other regions where the ends of the ribs are attached to the ends of the opposing ribs. Some plates may contain long ribs which enter grooves and some short ribs which abut ribs on the opposed plate.

Figure 9:
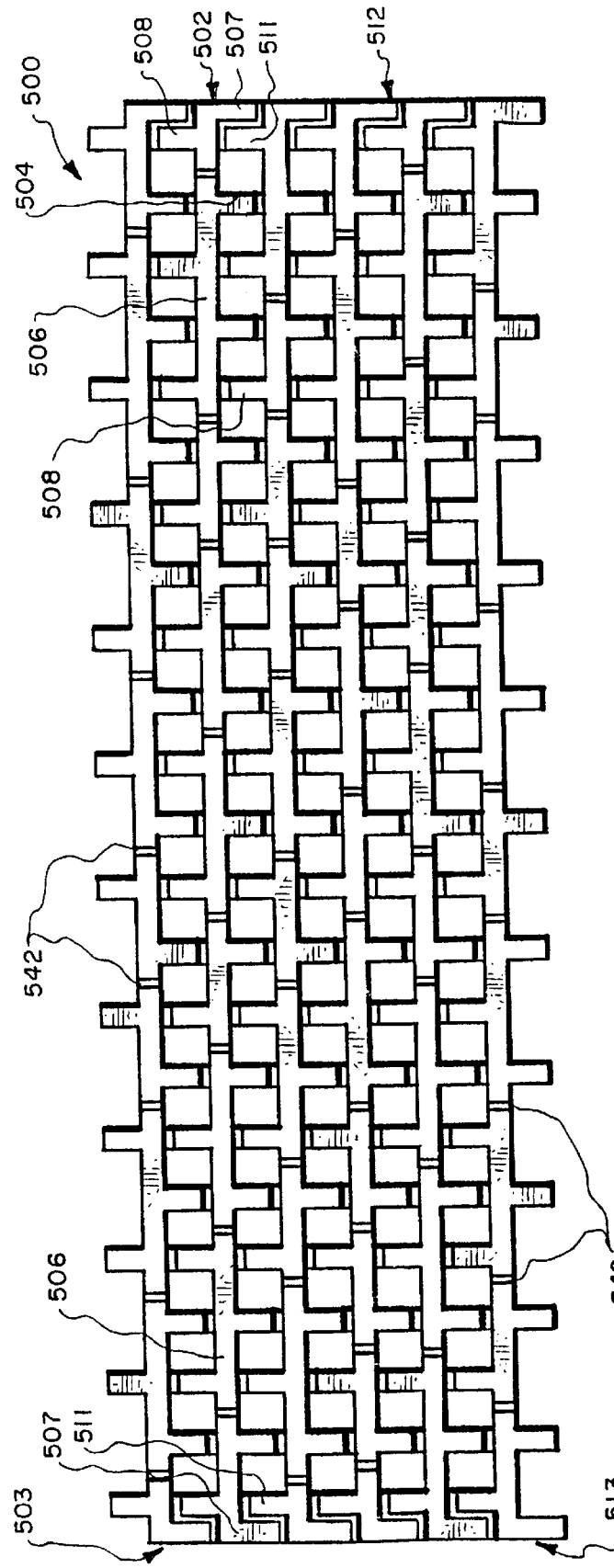
FIG. 9 is a front view in elevation of a stack of cured plates joined by a fugitive wrap.
Figure 10:
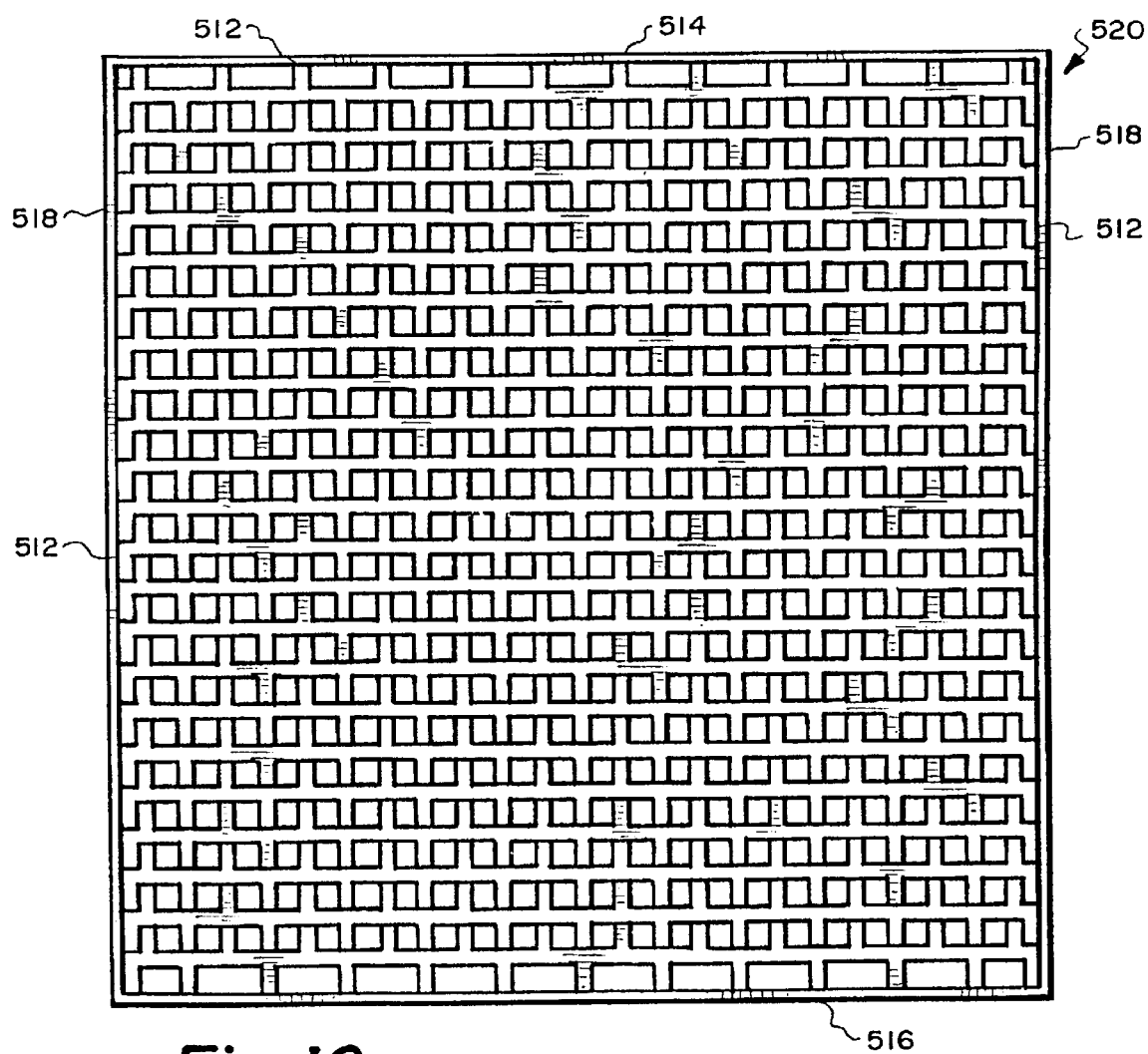
FIG. 10 is a front view in elevation of a stack of fired plates.

Elements in which the plates are adhered to each other, form a brittle ceramic body. Even though there is some freedom of movement where a rib does not adhere to the end of an opposed rib or to the inner surface of the central support, the element can still crack and crumble and degrade when repeatedly heated and cooled during regenerative thermal processing. The element 500 shown in FIGS. 9–10 is formed of interleaved plates 502, that are not adhered to each other by heat curing or by adhesive.

The plate 502 has a plurality of parallel ribs 504 extending downward from the central support 506. The end ribs 507 start and end coincident with the end of the central member. The ribs 508 extend upwardly from the central support 506. The end ribs 511 are indented from the edges 513 of the central support by about the width of an end rib 507. When the plates 502, 503 are stacked, the end ribs 507 are locked into the indented spaces which prevents the unadhered plates from sliding. The end ribs 507 in combination with the central supports 506 form end walls 512.

It would be time consuming to place each plate into a column. Furthermore, breakage can occur during handling of the individual plates or stacks of plates while they are filled into the shell of a RTO or catalytic column or a heat exchanger. As shown in FIG. 10, a stack of plates can be held together by wrapping the plates along the end walls 512 and across the top surface 514 and bottom surface 516 with a wrap 518 of strong plastic, preferably a shrink wrap such as Saran which is a vinyl acetate-vinylidene chloride copolymer. The element 520 can then be handled as a stable entity and placed in the column or on top of and/or adjacent similar stacked elements. When hot gases first enter the column, the wrap will decompose into gaseous products and will be exhausted from the column by the hot gases.

Figure 11:
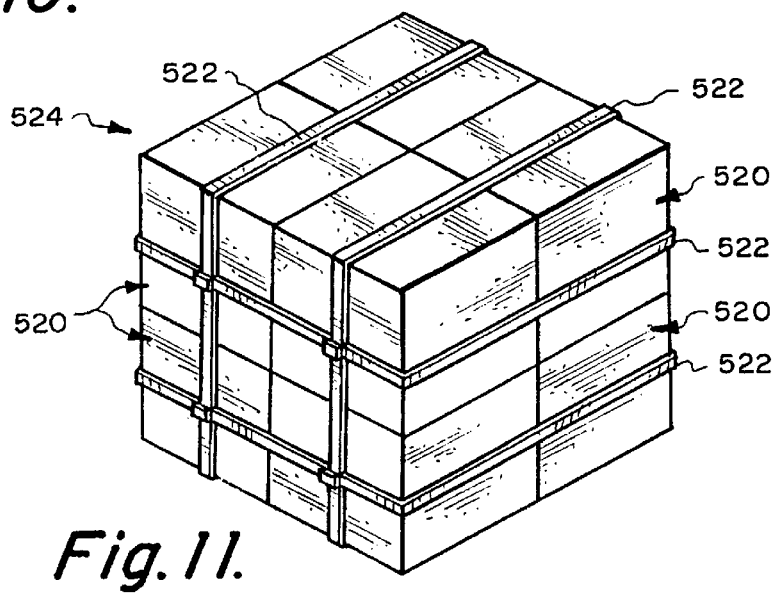
FIG. 11 is a perspective view of an assembly of elements adhered by metal bands.

In order to further speed filling of a column, not shown, a plurality of elements 520 can be joined together by metal straps 522 to form an assembly 524 as shown in FIG. 11.

The elements and modules can be assembled into assemblies of varying sizes and shapes. Preferably, the assembly has a rectangular column configuration or a cube configuration. The modules can be aligned with the side by side modules having channels parallel to each other and the end to end modules having the channels in the same axial alignment. Eight 6 inch cubical modules will form a 1 foot square cube assembly. Eighteen 4 inch cubical modules will also form a 1 foot cubical assembly.

Figure 12:
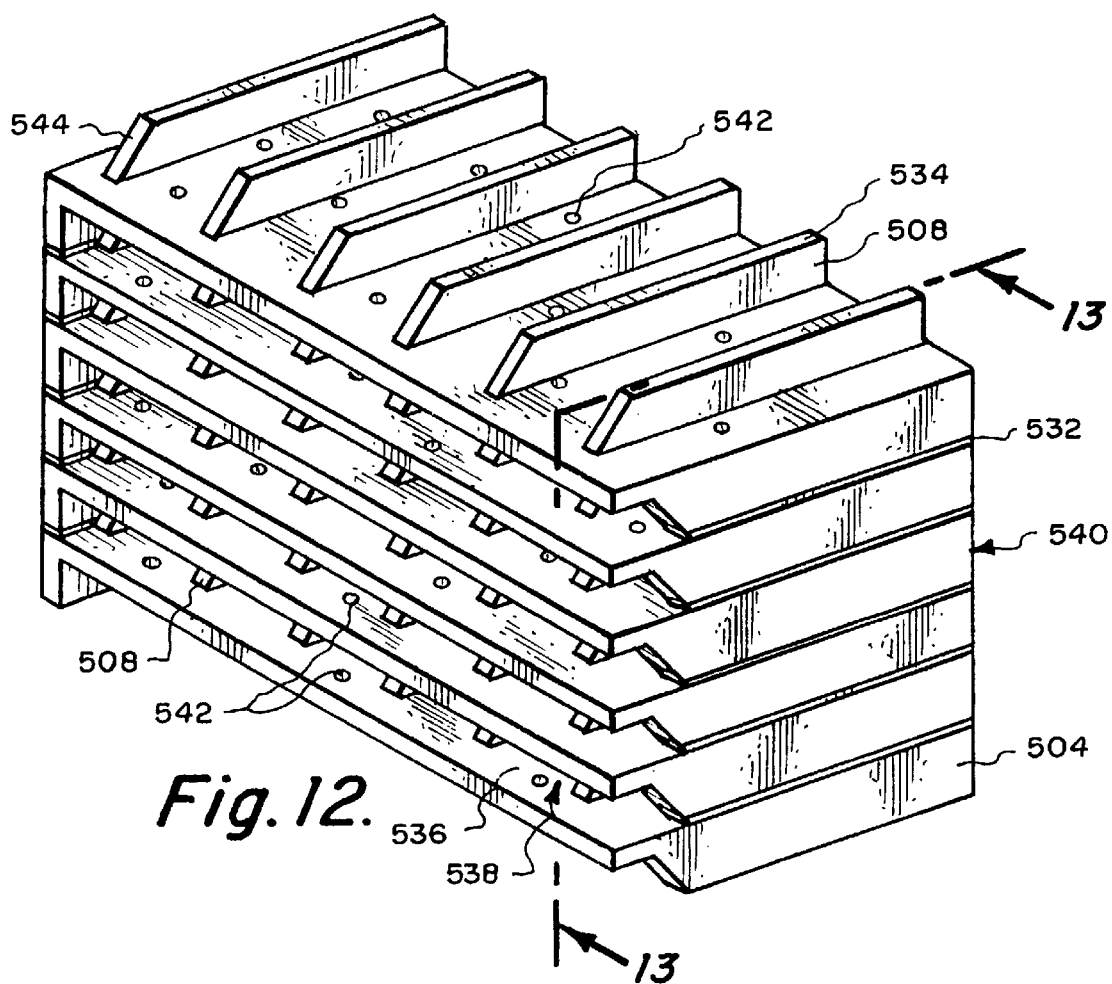
FIG. 12 is an isometric view of a further embodiment showing improvements to the stack.
Figure 13:
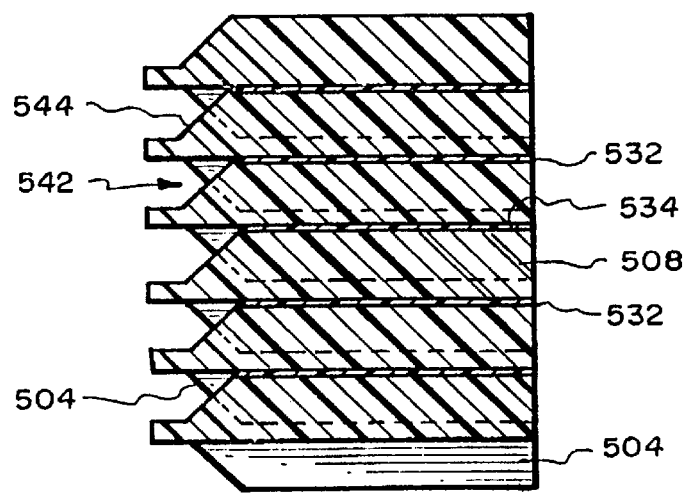
FIG. 13 is a view in section taken along line 13—13 of FIG. 12.

However, as discussed above, the use of organic films or adhesives contributes pollutants to the environment. Residual combustion products of the organic film can remain in the bed. As shown in FIGS. 12 and 13, the plates 540 are adhered together by applying a film of an aqueous solution of sodium or potassium silicate (water glass). Water will evaporate from the film during air drying at ambient temperature and sodium or potassium silicate bonds 532 will form at the points of contact between the end faces 534 of the ribs 508, 504 and the bottom surface 536 of the grooves 538.

The unbonded facing surfaces allow lateral transfer of the flowing gas between adjacent channels. This contributes to more efficient mixing of the gas and liquid, increasing the heat and mass transfer per volume of packing and lowers the pressure drop. Further improvements in efficiency of mixing and stress relief can be provided by forming apertures 546 in the plates to increase communication between adjacent channels. This will further lower the pressure drop as will widening the inlet openings 542 to the channels by removing a short section of rib 544.

A packing module according to FIG. 7 was prepared by air drying a stack of cured ceramic plates coated with water glass to form a module. The ribs were about 7.0 mm high with rounded ends and were spaced about 7.24 mm apart.

The module had the following dimensions and physical properties:

| Physical Dimensions | |
|---|---|
| Layer Thickness | 1.5 mm |
| Overall Module Dimensions | 12" × 12" × 4" |
| Specific Surface Area | 210 Ft$^2$/ft$^3$ |
| Weight | 72 Lbs/ft$^3$ |
| Void Fraction | 60% |
| Physical Properties | |
| Specific Gravity | 2.25–2.35 |
| Water Absorption (ASTM C373) | <0.5% |
| Acid Resistance Strength | |
| Wt. Loss (ASTM C279) | ≦4% |
| Maximum Working Temperature | 2,350° F. |
| Heat Capacity | 0.22 BTU/lb ° F. |
| Cold Crushing Strength | 15,000 lbs/ft$^2$ |

Figure 14:
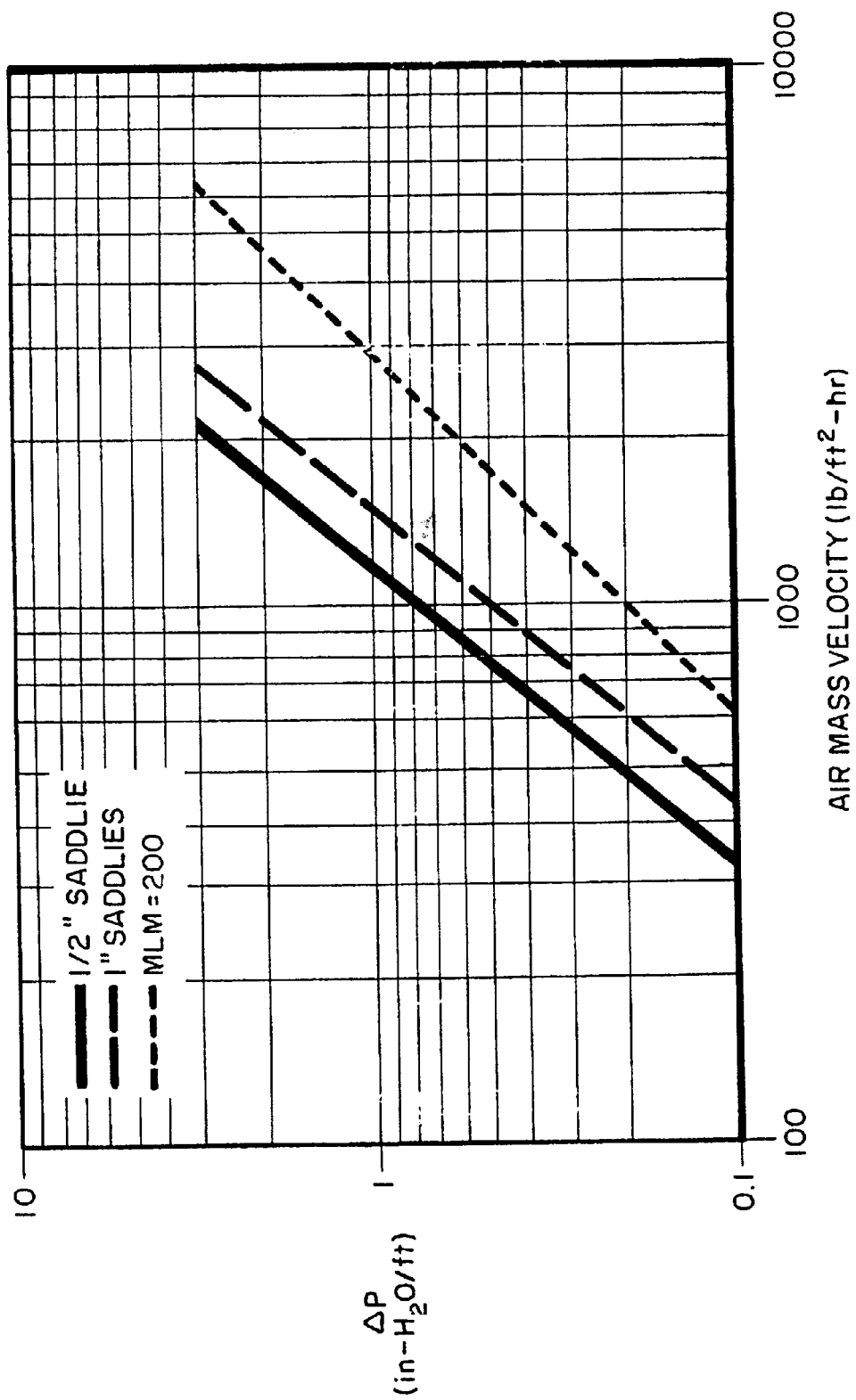
FIG. 14 is a Pressure Drop Comparison of the packing media of the invention, 1 inch saddles and monolith media.

The performance of the packing module of the invention was compared to ceramic monolith media and to 1 inch and ½ inch saddles. The data shown in FIG. 14 is a pressure drop comparison of the three packing media utilizing an air flow at 70° F.

The media depth to achieve 95% RTO Heat Recovery at 200 fpm for saddles is almost 2⅔ as much as the inventive media and the media depth for monolith is 1⅔ as much as the MULTI-LAYER MEDIA (MLM) media of the invention.

The MLM media of the invention is the most efficient and cost-effective heat-recovery media for regenerative thermal oxidization (RTO) systems. Operating data confirms that MLM is the first substantial improvement over 1 inch saddles and monolith in decades. MLM provides extremely high thermal efficiencies. The new MLM packing outperforms all other ceramic media in heat exchange, energy efficiency and pressure drop. It reduces capital and operating costs. MLM has been field and laboratory tested, and the results have been outstanding. MLM heats up and cools down faster; compared with saddles, the thin, layered shape of MLM has much more of its material within 1 mm of the surface. Also, because of the inter-connected channels (as opposed to isolated single channels in monolith) gas flows in all directions. This will enhance heat transfer as well as reduce plugging tendencies. MLM packing is an engineering breakthrough. With the reduced operating and capital costs, and greater efficiency, MLM will soon pay for itself.

MLM packing material is believed to be one of the greatest advances in packing design in decades, providing flexibility in design variations. MLM can be utilized in RTO and is also useful in mass transfer applications involving corrosive streams and high temperature such as absorption and drying in a sulfuric acid plant, mining, mineral recovery, leaching, dissolving, absorption in a petrochemical plant.

It is to be realized that only preferred embodiments of the invention have been described and that numerous substitutions, modifications and alterations are permissible without departing from the spirit and scope of the invention as defined in the following claims.

We claim:

1. A ceramic packing element comprising:
    a stack of individual ceramic plates;
    a first plate having a first surface including a plurality of parallel ribs forming a plurality of parallel grooves between the ribs, a plurality of the ribs having end surfaces in a common plane;
    a second plate having a first surface in close contact with the end surfaces of the ribs in a common plane on the first plate to form parallel channels; and
    a layer of inorganic adhesive on at least one of said surfaces for adhering said surfaces together.

2. A ceramic packing element according to claim 1 in which the spacing between ribs is greater than the width of an opposed rib and the ribs on opposed surfaces are interleaved with the outer end of each rib adhered to the first surface of the opposed plate.

3. A ceramic packing element according to claim 1 in which the ribs on the first surface of the second plate are spaced further apart than the ribs on the first surface of the first plate and at least some of said ribs interleave and seat on the bottom surface of the opposed grooves.

4. A packing element according to claim 1 in which the channels have an enlarged inlet.

5. A ceramic packing assembly comprising a plurality of packing elements as defined in claim 1 placed into an assembly with their channels in alignment and means securing the elements together.

6. An assembly according to claim 5 in which the securing means comprises metal bands.

7. A ceramic packing element according to claim 1 in which the inorganic adhesive is water glass.

8. A ceramic packing element according to claim 7 in which the water glass is selected from silicates of the group consisting of sodium and potassium.

9. A method of forming a ceramic packing element comprising the steps of:
    forming in a first surface of a ceramic plate a plurality of parallel ribs a plurality of which have end surfaces in a common plane, and parallel grooves having bottom surfaces in a common plane, formed therebetween;
    forming a layer of inorganic adhesive on at least one of said end surfaces and bottom surfaces;
    placing the end surfaces in engagement with the bottom surfaces to close said grooves to form channels; and
    curing said adhesive to adhere said surfaces together.

10. A method according to claim 9 in which the ceramic elements are in the cured state.

11. A method according to claim 9 in which the inorganic adhesive is water glass.

12. A method according to claim 11 in which the water glass is selected from silicates of the group consisting of sodium and potassium.

* * * * *